United States Patent
Stefu et al.

(10) Patent No.: US 12,295,818 B2
(45) Date of Patent: May 13, 2025

(54) SANITARY ARTICLE WITH REMOVABLE LATERAL AND/OR END PORTIONS

(71) Applicant: EASYDAY HEALTH PRODUCTS INC., Blainville (CA)

(72) Inventors: Cristian Stefu, Blainville (CA); Ioana Mihaela Hidisan, Blainville (CA); Regent Racine, Blainville (CA)

(73) Assignee: EASYDAY HEALTH PRODUCTS INC., Blainville (CA)

( * ) Notice: Subject to any disclaimer, the term of this patent is extended or adjusted under 35 U.S.C. 154(b) by 839 days.

(21) Appl. No.: 17/419,015

(22) PCT Filed: Dec. 30, 2019

(86) PCT No.: PCT/CA2019/000174
§ 371 (c)(1),
(2) Date: Jun. 28, 2021

(87) PCT Pub. No.: WO2020/132740
PCT Pub. Date: Jul. 2, 2020

(65) Prior Publication Data
US 2022/0110800 A1     Apr. 14, 2022

Related U.S. Application Data

(60) Provisional application No. 62/786,054, filed on Dec. 28, 2018.

(51) Int. Cl.
*A61F 13/474*     (2006.01)
*A61F 13/476*     (2006.01)
*A61F 13/505*     (2006.01)
*A61F 13/84*      (2006.01)

(52) U.S. Cl.
CPC .......... *A61F 13/474* (2013.01); *A61F 13/476* (2013.01); *A61F 13/505* (2013.01); *A61F 2013/8497* (2013.01)

(58) Field of Classification Search
CPC .... A61F 13/474; A61F 13/476; A61F 13/493; A61F 13/505; A61F 2013/49063; A61F 2013/49066; A61F 2013/5055; A61F 2013/8497
See application file for complete search history.

(56) References Cited

U.S. PATENT DOCUMENTS

| | | | | |
|---|---|---|---|---|
| 5,704,929 A | * | 1/1998 | Bien | A61F 13/474 604/387 |
| 6,524,290 B2 | * | 2/2003 | Motta | A61F 13/505 604/385.01 |
| 8,105,302 B2 | * | 1/2012 | Rubio | A61F 13/47236 604/385.01 |

(Continued)

*Primary Examiner* — Catharine L Anderson
*Assistant Examiner* — Lynne Anderson
(74) *Attorney, Agent, or Firm* — PRAXIS (57) ABSTRACT

A sanitary article comprises a longitudinal main body bounded by a perimeter defining opposite ends and opposite lateral margins and comprising a body contacting surface and an opposite outer surface. At least one removable portion extends from at least one segment of the perimeter. A tear line is defined between at least one removable portion and the at least one segment for providing selective detachment therebetween. The at least one segment of the perimeter is positioned at an opposite end and/or an opposite lateral margin.

6 Claims, 6 Drawing Sheets

(56) References Cited

U.S. PATENT DOCUMENTS

| | | | |
|---|---|---|---|
| 10,478,351 B2* | 11/2019 | Alligood | A61F 13/474 |
| 2002/0143315 A1* | 10/2002 | Garrad | A61F 13/476 604/385.04 |

* cited by examiner

SANITARY ARTICLE WITH REMOVABLE LATERAL AND/OR END PORTIONS

CROSS-REFERENCE TO RELATED APPLICATIONS

The present application claims priority on U.S. Provisional Patent Application Ser. No. 62/786,054 filed on Dec. 28, 2018 and which is incorporated by reference herein in its entirety.

TECHNICAL FIELD

The present disclosure generally relates to sanitary articles are as incontinence or human discharge protectors and are also in used feminine hygiene such as sanitary napkins or pads or incontinence napkins. More particularly but not exclusively the present disclosure relates to sanitary article with removable lateral and/or end portions.

BACKGROUND

Sanitary articles are usually disposable absorbent articles designed to be worn externally of the body by a user and to receive fluids discharged from the body. Sanitary articles are used in feminine hygiene and they include sanitary napkins or pads. Sanitary articles also include incontinence napkins. Sanitary articles include panty liners, incontinence protectors and diapers. A sanitary napkin or pad is an absorbent sanitary article worn by a woman while menstruating, recovering from vaginal surgery, for lochia, after an abortion, or in any other situation where it is necessary to absorb a flow of blood from the vagina. These articles may also be used for incontinence. Of course, incontinence issues can also be managed by other sanitary articles such as incontinence napkins or pads. A sanitary article prevents soiling of the wearers clothing by such discharges. Sanitary articles include a body contacting side and a garment contacting side. Many sanitary articles have lateral portions such as wings, other do not have any laterally extending portions and users must choose between these available versions.

OBJECTS

An object of the present disclosure is to provide a sanitary article.

An object of the present disclosure is to provide a sanitary article with removable lateral and/or end portions.

SUMMARY

In accordance with an aspect of the disclosure, there is provided a sanitary article comprising: a longitudinal main body bounded by a perimeter defining opposite ends and opposite lateral margins and comprising a body contacting surface and an opposite outer surface; at least one removable portion extending from at least one segment of the perimeter; and a tear line defined between at least one removable portion and the at least one segment for providing selective detachment therebetween.

In an embodiment of this sanitary article, the at least one removable portion comprises at least one inner tear line thereby providing selective detachment of at least one part thereof therefrom. In an embodiment, the at least one part comprises indicia. In an embodiment, the at least one removable portion comprises a plurality of inner tear lines thereby providing selective detachment of a plurality of parts thereof therefrom. In an embodiment, each of the plurality of parts comprises respective indicia.

In an embodiment of this sanitary article, the at least one segment of the perimeter is positioned at one of the opposite lateral margins of the main body. In an embodiment, the at least one segment of the perimeter is positioned at one of the opposite ends of the main body.

In an embodiment, the sanitary article further comprises a plurality of removable portions, wherein each of the removable portions extends from a respective segment of the perimeter defining a respective tear line therebetween for providing selective detachment therebetween. In an embodiment, one or more of the plurality of removable portions comprises at least one inner tear line thereby providing selective detachment of at least one part thereof therefrom. In an embodiment, the at least one part comprises indicia. In an embodiment, one or more of the plurality of removable portions comprises a plurality of inner tear lines thereby providing selective detachment of a plurality of parts thereof therefrom. In an embodiment, each of the plurality of parts comprises respective indicia. In an embodiment, at least two of the respective segments of the perimeter are respectively positioned at each of the opposite lateral margins of the main body. In an embodiment, at least two of the respective segments of the perimeter are respectively positioned at each of the opposite ends of the main body.

In accordance with another aspect of the present disclosure, there is provided a sanitary article comprising: a longitudinal main body bounded by a perimeter defining opposite ends and opposite lateral margins and comprising a body contacting surface and an opposite outer surface; at least one removable portion extending from at least one segment of the perimeter and comprising at least one inner tear line thereby providing selective detachments of at least one part thereof therefrom.

In an embodiment of the sanitary article in accordance with another aspect of the disclosure, the at least one part comprises indicia. In an embodiment, the at least one removable portion comprises a plurality of inner tear lines thereby providing selective detachment of a plurality of parts thereof therefrom. In an embodiment, each of the plurality of parts comprises respective indicia In an embodiment of the sanitary article in accordance with another aspect of the disclosure, a tear line is defined between the at least one removable portion and the at least one segment of the perimeter for providing selective detachment therebetween. In an embodiment, the at least one segment of the perimeter is positioned at one of the opposite lateral margins of the main body. In an embodiment, the at least one segment of the perimeter is positioned at one of the opposite ends of the main body.

In an embodiment of the sanitary article in accordance with another aspect of the disclosure, the sanitary article further comprises a plurality of removable portions, wherein each of the removable portions extends from a respective segment of the perimeter, wherein at least two of the plurality of removable portions respectively comprise at least one inner tear line thereby providing selective detachment of at least one respective part thereof therefrom. In an embodiment, the at least one respective part comprises indicia. In an embodiment, one or more of the plurality of removable portions comprises a plurality of inner tear tines thereby providing selective detachment of a plurality of parts thereof therefrom. In an embodiment, each of the plurality of parts comprises respective indicia. In an embodiment, at least two of the respective segments of the perimeter are respectively positioned at each of the opposite lateral margins of the main body. In an embodiment, at least two of the respective segments of the perimeter are respectively positioned at each of the opposite ends of the main body. In an embodiment, a respective lateral tear line is defined between the at least two of the plurality of removable portions and the at least two segments of the perimeter for providing selective detachment therebetween.

In accordance with an embodiment of either one of the above described sanitary articles, the body contacting surface is liquid pervious and/or the outer side of the main body is liquid impervious and/or the outer side is a garment contacting side and/or the outer side comprises an adhesive for adhering to a garment.

In accordance with an embodiment of either one of the above described sanitary articles, the sanitary article further comprises an absorbent core between the body contacting surface and the outer surface.

In accordance with an embodiment of either one of the above described sanitary articles, the removable portion defines inner and outer sides thereof, the removable portion inner side being contiguous with the body contacting surface the removable portion outer side being contiguous with the outer surface.

In accordance with a further aspect of the present disclosure, there is provided a sanitary article comprising: a longitudinal main body defining opposite ends and opposite lateral margins and comprising a liquid pervious body contacting surface, an opposite liquid impervious garment contacting surface and an absorbent core therebetween; and a pair of lateral portions, each lateral portion extending from a respective one of the lateral margins, a lateral tear line defined between at least one of the lateral portions and the respective one of the lateral margins for providing selective detachment therebetween.

In an embodiment of the sanitary article according to this further aspect of the disclosure, another lateral tear line is defined between the other of lateral portions and the respective other one of the lateral margins for providing selective detachment therebetween.

In an embodiment of the sanitary article according to this further aspect of the disclosure, at least one of the lateral portions comprises at least one inner tear line thereby providing selective detachments of at least one part thereof therefrom. In an embodiment, the at least one part comprises indicia. In an embodiment, at least one of the lateral portions comprises a plurality of inner tear lines thereby providing selective detachment of a plurality of parts thereof therefrom. In an embodiment, each of the plurality of parts comprises respective indicia.

In accordance with yet another aspect of the present disclosure, there is provided a sanitary article comprising: a longitudinal main body defining opposite ends and opposite lateral margins and comprising a liquid pervious body contacting surface, an opposite liquid impervious garment contacting surface and an absorbent core therebetween; and a pair of lateral portions, each lateral portion extending from a respective one of the lateral margins, at least one of the lateral portions comprises at least one inner tear line thereby providing selective detachments of at least one part thereof therefrom.

In an embodiment of the sanitary articles in accordance with both of the further and the yet another aspects of the disclosure, the at least one part comprises indicia.

In an embodiment of the sanitary articles in accordance with both of the further and the yet another aspects of the disclosure, at least one of the lateral portions comprises a plurality of inner tear lines thereby providing selective detachment of a plurality of parts thereof therefrom. In an embodiment, each of the plurality of parts comprises respective indicia.

In an embodiment of the sanitary articles in accordance with both of the further and the yet another aspects of the disclosure, at least a lateral tear line is defined between at least one of the lateral portions and the respective one of the lateral margins for providing selective detachment therebetween. In an embodiment, another lateral tear line is defined between the other of lateral portions and the respective other one of the lateral margins for providing selective detachment therebetween.

In an embodiment of the sanitary articles in accordance with both of the further and the yet another aspects of the disclosure, the garment contacting surface comprises an adhesive material for adhering to at least a portion of an undergarment worn by a user. In an embodiment, the lateral portions comprise an adhesive substance for adhering to at least a portion of an undergarment worn by a user. In an embodiment, the lateral portions are selected from the groups consisting of wings, flaps, extensions and combinations thereof.

Other objects, advantages and features of the present disclosure will become more apparent upon reading of the following non-restrictive description of illustrative embodiments thereof, given by way of example only with reference to the accompanying drawings.

DETAILED DESCRIPTION OF ILLUSTRATIVE EMBODIMENTS

Generally stated and in accordance with an aspect of the present disclosure, there is provided a there is provided a sanitary article comprising a longitudinal main body bounded by a perimeter defining opposite ends and opposite lateral margins and comprising a body contacting surface and an opposite outer surface. At least one removable portion extends from at least one segment of the perimeter. In an embodiment, a tear line is defined between at least one removable portion and the at least one segment for providing selective detachment therebetween. In an embodiment, the at least one removable portion comprises at least one inner tear line thereby providing selective detachments of at least one part thereof therefrom Generally stated and in accordance with an aspect of the present disclosure, there is provided a sanitary article comprising a longitudinal main body defining opposite ends and opposite lateral margins and comprising a liquid pervious body contacting surface, an opposite liquid impervious garment contacting surface and an absorbent core therebetween. A pair of lateral portions respectively extend from a respective one of the lateral margins. In an embodiment, a lateral tear line is defined between at least one of the lateral portions and the respective one of the lateral margins for providing selective detachment therebetween. In an embodiment, at least one of the lateral portions comprises at least one inner tear line thereby providing selective detachments of at least one part thereof therefrom.

Figure 1:
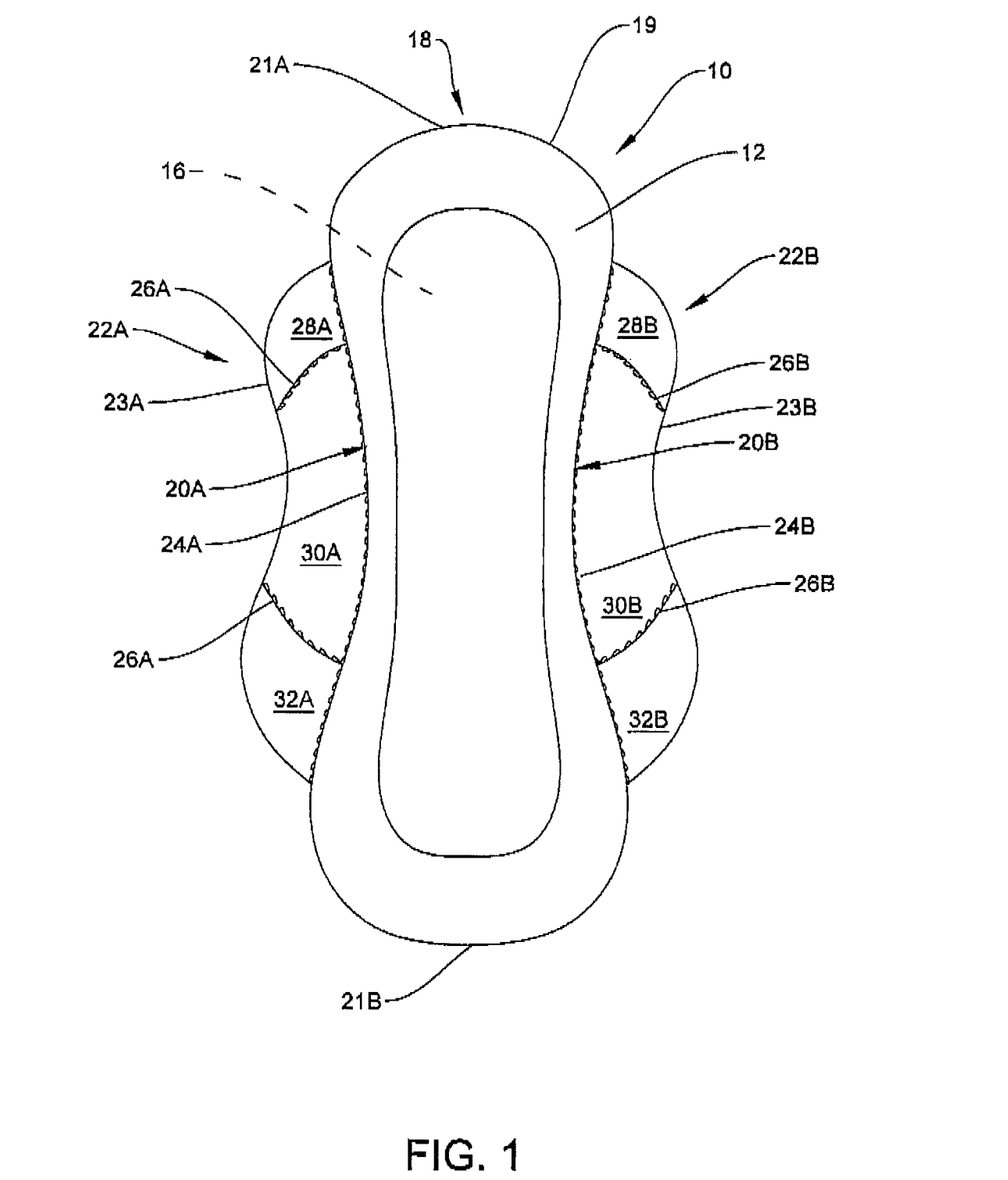
FIG. 1 is a top view of the sanitary article in accordance with a non-restrictive illustrative embodiment of the present disclosure.
Figure 2:
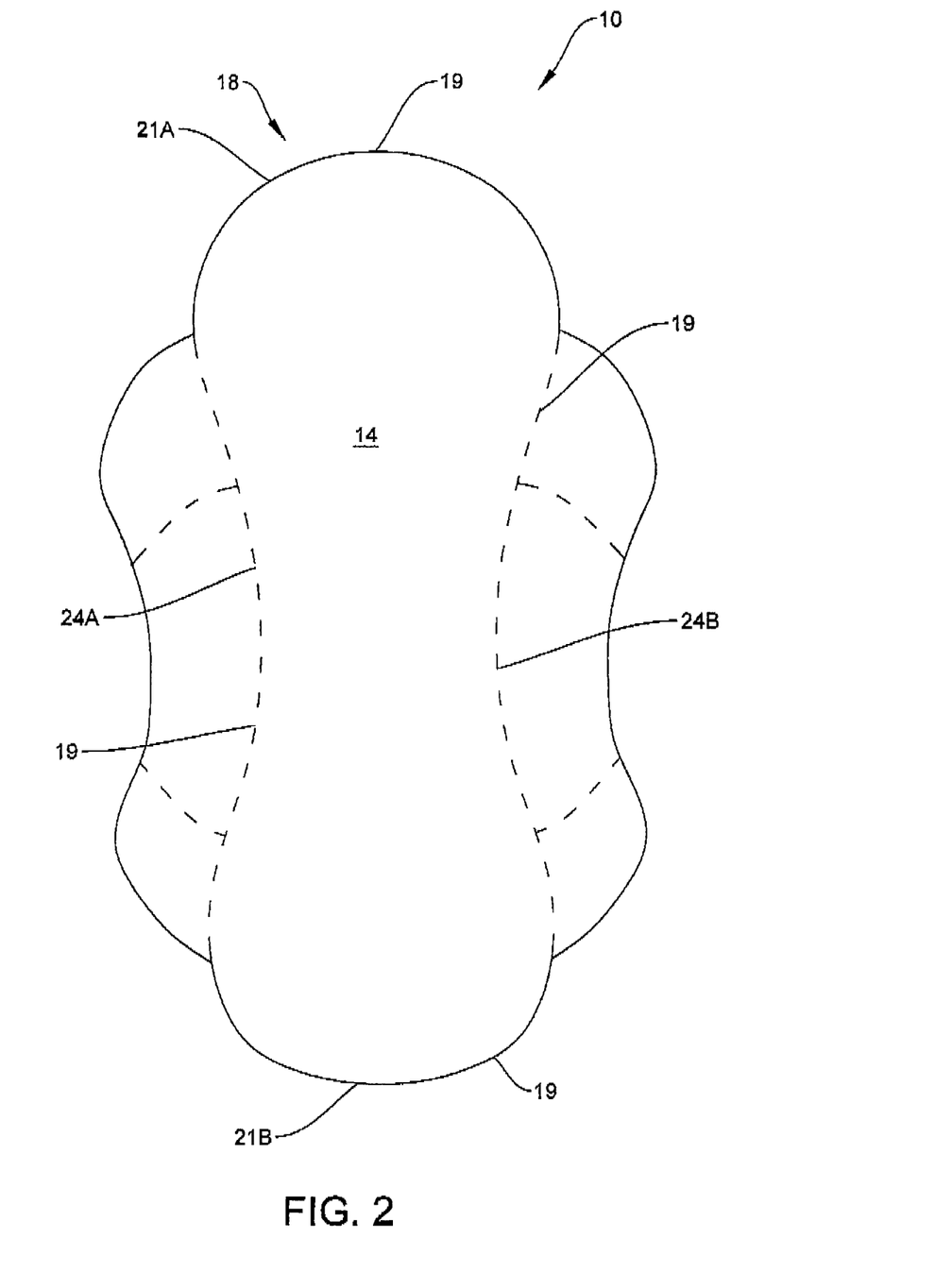
FIG. 2 is a bottom view of the sanitary article of FIG. 1.

FIGS. 1 and 2 show the sanitary article 10, including a top surface 12 sheet 12, a backing sheet 14 and core 16 therebetween.

In an embodiment, the top sheet 12 is liquid pervious and defines the body contacting side or surface of the sanitary article 10. The backing sheet 14 is liquid impervious thereby acting as a protective barrier. The backing sheet 14 defines an outer side such as a garment (or undergarment) contacting side or surface. In an embodiment, this surface adheres to the wearers undergarment via an adhesive. Adhesives such as pressure sensitive adhesives are suitable for this purpose. The core 18 is an absorbent core that absorbs discharge. In an embodiment the body contacting surface of the sanitary article 10 may also include an adhesive to adhere to the body of the user.

The top sheet 12 is made of materials which are compliant and readily conform to the shape of the body. The top sheet 12 may exhibit good strikethrough and rewet characteristics, permitting bodily discharges to rapidly penetrate therethrough to the core 16, but not flow back to the skin of the wearer. The top sheet 12 may be porous to permit discharged liquids to pass through to the core 16. The body contacting surface provides comfortable and dry-feeling contact with body surfaces while allowing free passage of fluids therethrough into the absorbent core 16.

The backing sheet 14 prevents discharges absorbed by the core 16, from escaping. The backing sheet 14 prevents the fluids which are expelled, or which escape from the absorbent core 16 from soiling the user's garments.

The absorbent core 16 is intermediate the top sheet 12 and the backing sheet 14 and the article 10 is integrally or unitarily assembled. Therefore, the body contacting surface of the article 10 is defined by the top sheet 12 and the opposite protective barrier or garment contacting surface is defined by the backing sheet 14. The absorbent core 16 has two opposed faces, one oriented towards the backing sheet 14 and one oriented towards the top sheet 12. The absorbent core 16 provides for receiving, collecting and containing bodily discharges such as menses, deposited thereon or which pass through the top sheet 12. In an embodiment, the core 16 is configured to be narrow and thin so as to be comfortable to the wearer.

The article 10 defines a longitudinal main body 18 comprising the top sheet 12, the backing sheet 14 and the absorbent core 16. The main body 18 is delimited or bounded by a perimeter 19 that defines opposite lateral sides or margins 20A and 20B and opposite ends 21A and 21B. The opposite lateral margins 20A and 20B run along the longitudinal length of the main body 18. The opposite lateral margins 20A and 20B define the width of the body portion 18 whereas the ends 21A and 21B define the length of the body portion 18.

The article 10 comprises such as lateral portions such as a pair of wings or flaps 22A and 22B which extend beyond each margin 20A and 20B. Each later portion 22A and 22B respectively and define a respective outer free edge 23A and 23B.

The lateral portions 22A and 22B may extend along the longitudinal length or segment of each margin 20A and 20B. The lateral portions 22A and 22B may be contiguous with the backing sheet 14, contiguous with the top sheet 12 or a laminate of both the top sheet 12 and the backing sheet 14. Each lateral portion 22A and 22B has a garment contacting face or portion that contacts the wearer's undergarments in use which may also include an adhesive material. The lateral portions 22A and 22B may be provided in a variety of suitable shapes and when in use extend beyond the undergarment crotch portion to be flipped thereunder and adhered to the outer surface of the undergarment opposite the body contacting surface thereof.

Figure 3:
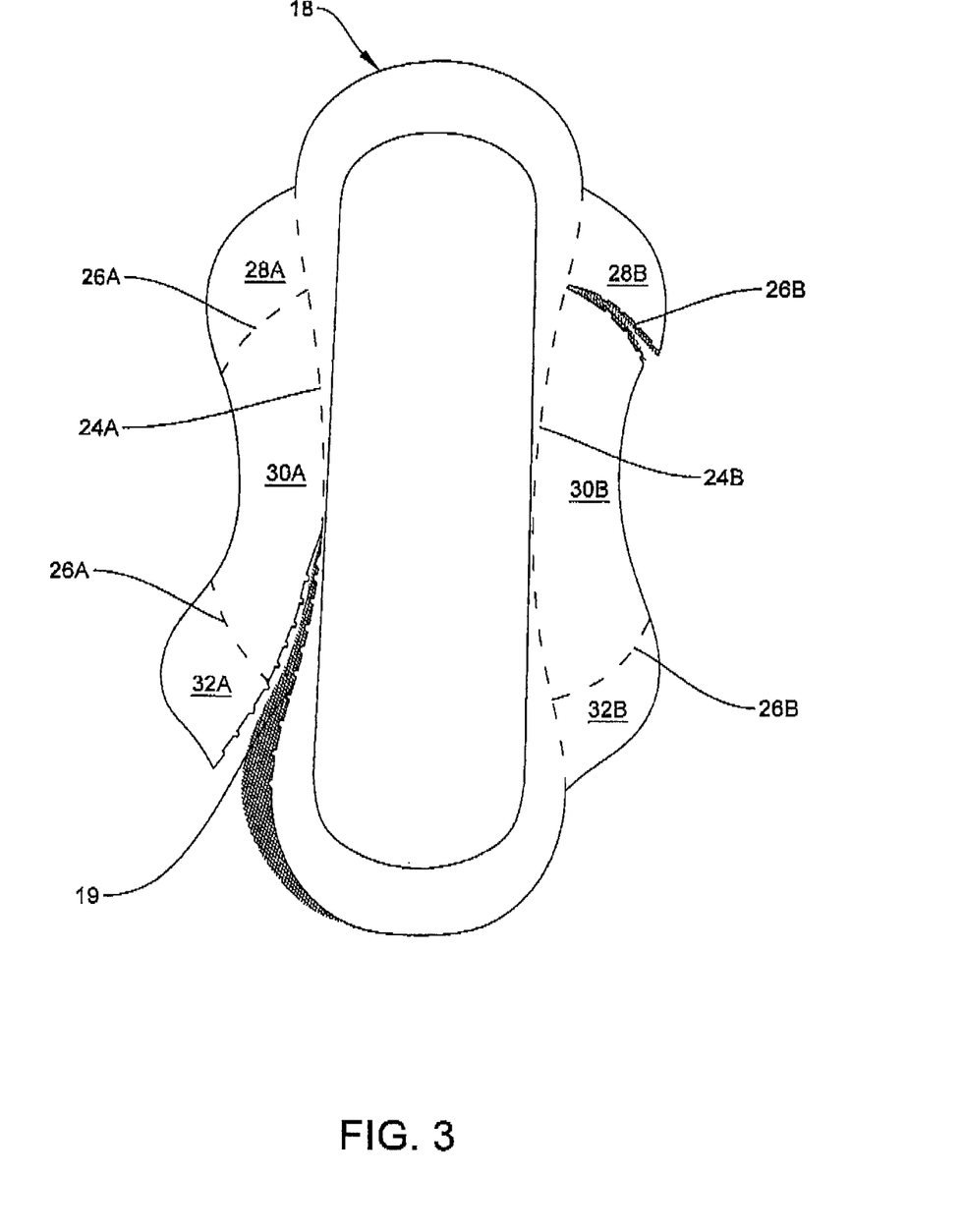
FIG. 3 is a top view of the sanitary article of FIG. 1 showing lateral portions thereof in the process of being removed in accordance with another non-restrictive illustrative embodiment of the present disclosure.
Figure 4:
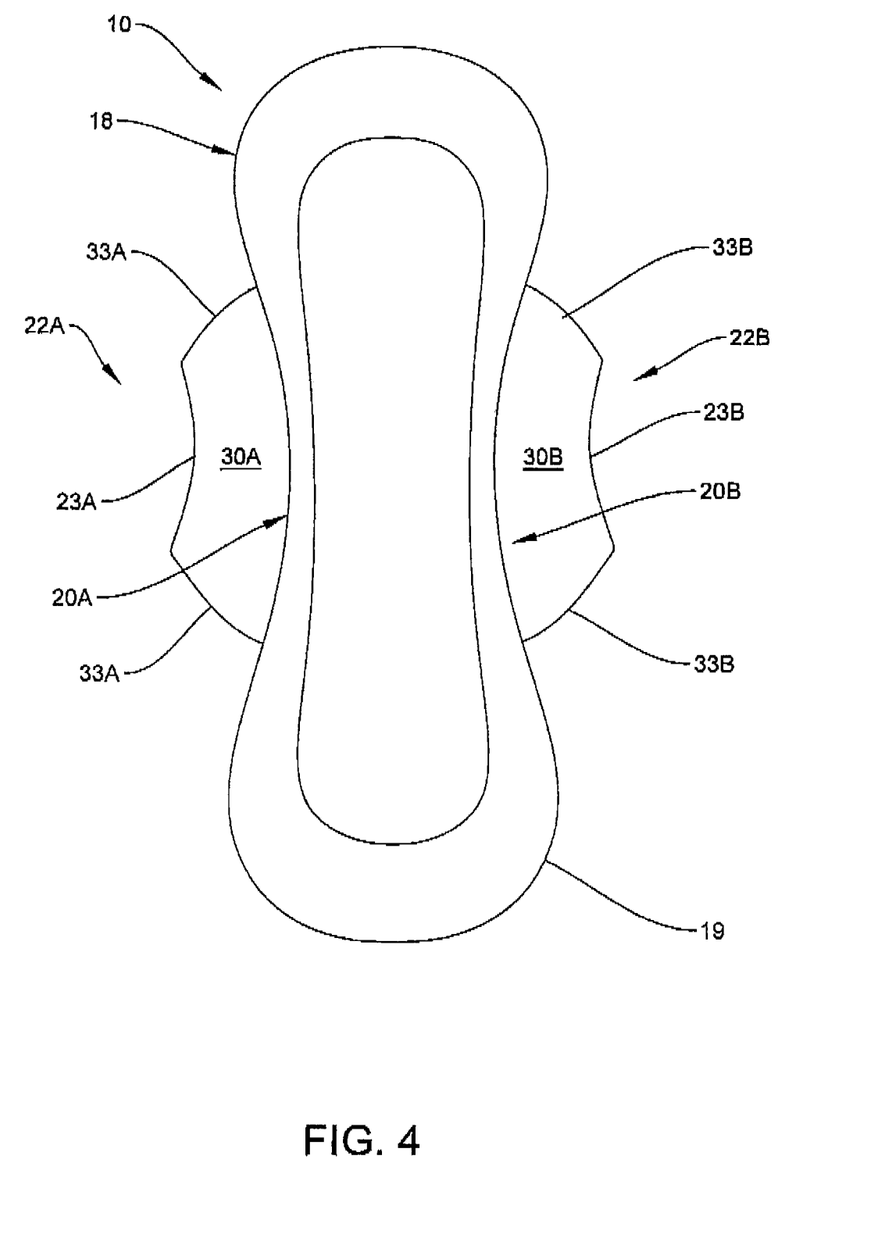
FIG. 4 is a top view of the sanitary article of FIG. 1 showing lateral portions thereof partially removed in accordance with another non-restrictive illustrative embodiment of the present disclosure.
Figure 5:
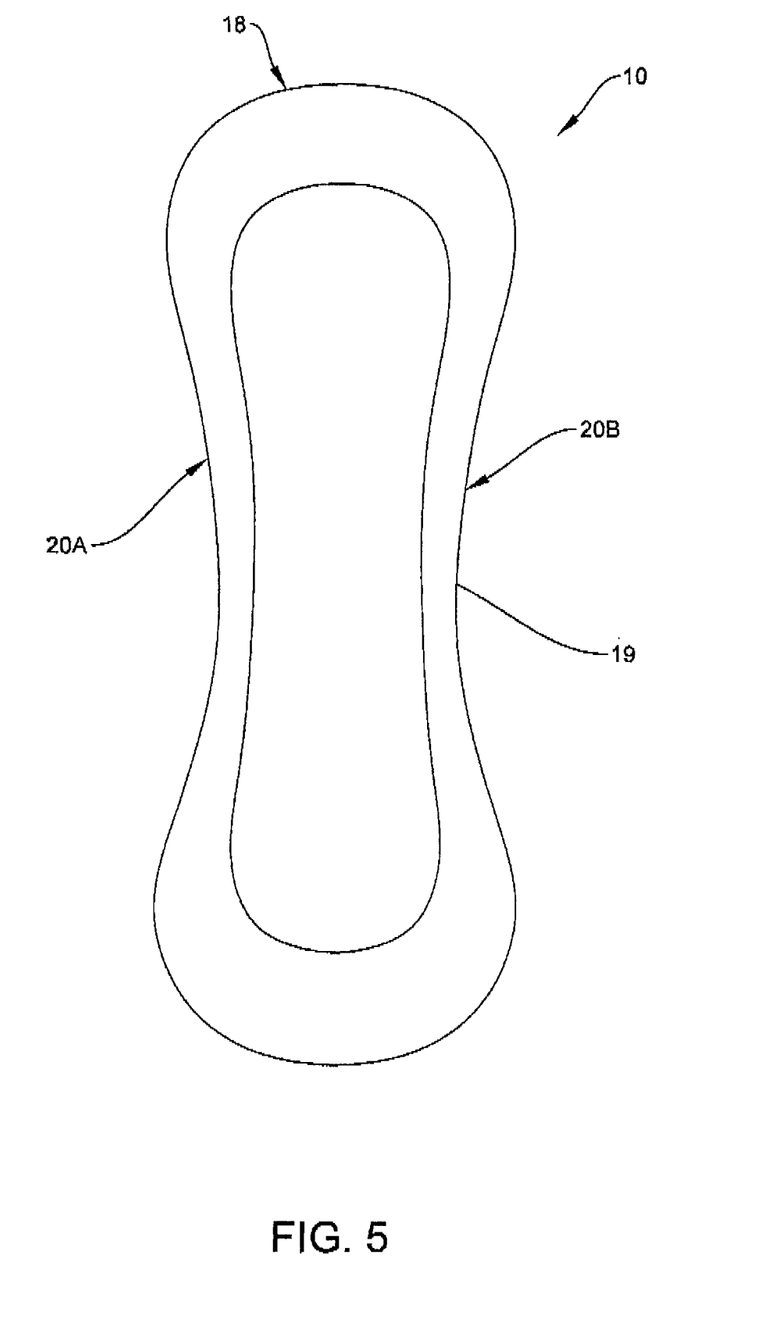
FIG. 5 is a top view of the sanitary article of FIG. 1 showing lateral portions thereof fully removed in accordance with another non-restrictive illustrative embodiment of the present disclosure.

With reference to FIGS. 1, 2 and 3, a respective tear line 24A and 24B is formed between each lateral portions 22A and 22B and its respective adjacent margin 20A and 20B providing the user to fully remove each lateral portion from the main body portion 18 as shown in FIG. 5. The tear line 24A or 248 provides the user with detaching the lateral portion 22A or 22B from along the length of the tear line 24A or 248 without disturbing the physical integrity of the margins 20A or 2B. Thus, when the lateral portions 22A and 22b are fully removed, the margins 20A and 20B are left free defining the lateral edges of the article Respective tear lines 26A and 26B are formed within each lateral portion 22A and 22B thereby defining parts or sub-parts thereof. In this example, lateral portion 22A defines three separately removable parts, 28A, 30A and 32A formed between tear lines 24A, 26A and the outer edge 23A. Similarly, lateral portion 22B defines three separately removable parts, 28B, 30B and 32B formed between tear lines 24B, 26B and the outer edge 23B. Each part 28A, 30A and 32A can be selectively and separately removed from lateral portion 22A. Similarly, each part 28B, 30B and 32B can be selectively and separately removed from lateral portion 226. For example, FIG. 4 shows that parts 28A and 32A have been removed from lateral portion 22A and parts 28B and 32B have been removed from lateral portion 22B, leaving parts 30A and 30B extending from the margins 20A and 20B and defining a remaining portions of the outer edges 23A and 23B as well as free edges 33A and 33B, respectively.

A variety of suitable sizes and configurations for each lateral portion 22A and 22B can be provided within the context of the present description. Moreover, the lateral portions 22A and 2B can be further divided via additional tear lines therein into a varying number of parts with variety of suitable sizes and configurations.

As such, a user may selectively remove either one or both of the lateral portions 22A and 22B. A user may selectively remove parts of one or both of the lateral portions 22A and 22B.

The parts of the lateral portions 22A and 22B may also include indicia in order to prompt the user to remove the parts so as to modulate the size or the configuration of the lateral portions as desired or as required.

Considering various activities of a user, she may choose a sanitary pad with or without wings or with bigger or smaller wings or differently shaped wings thus the tear lines. The present sanitary article provides these options without recourse to different articles to meet different needs dependent on various activities. Moreover, with respect to incontinence issues some women prefer no wings, this is also true for some in the summer when dressed in lighter clothing. As such, the present sanitary articles provide these options based on user preferences.

Figure 6:
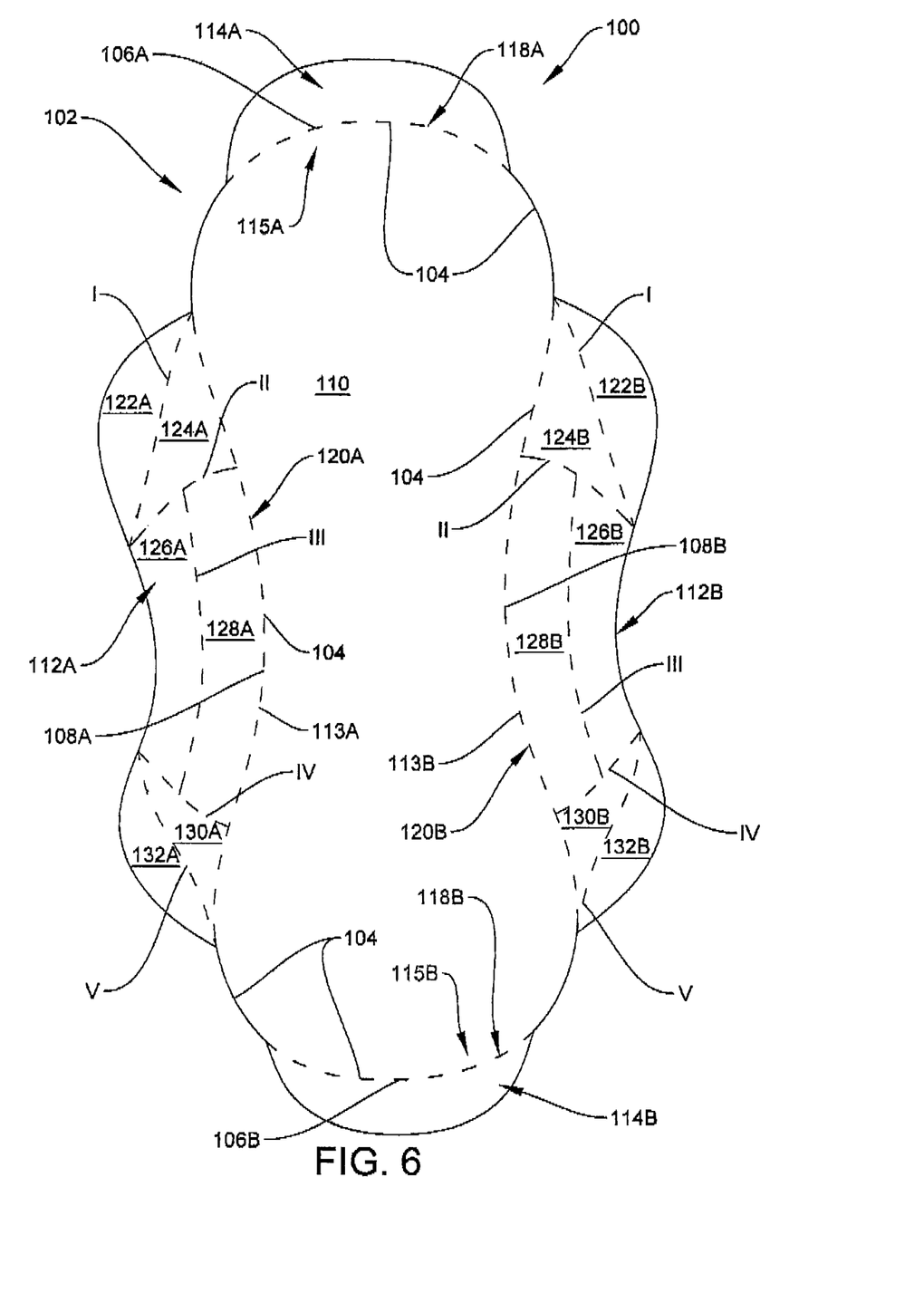
FIG. 6 is a top view of a sanitary article in accordance with a non-restrictive illustrative embodiment of the present disclosure.

Turning now to FIG. 6, there is shown a sanitary article 100, which can be an incontinence article or a diaper for example, Article 100 is similar but not identical to article 10 and comprises a main longitudinal body 102 delimited or bounded by a perimeter 104. The perimeter 104 defines opposite longitudinal ends or end margins 106A and 106B and opposite lateral sides or lateral margins 108A and 108B. The main body 102 defines a body contacting surface 110 and an opposite outer surface (not shown but similar to surface 14 for article 10).

Removable portions 112A, 112B, 114A, 1148 respectively extend from segments 113A, 113B, 115A, 115B of the perimeter 104. Segments 113A and 113B are positioned at respective lateral sides or lateral margins 108A and 108B. Segments 115A and 115B are positioned at respective longitudinal ends or end margins 106A and 106B. Tear line 118A is defined between the removable portion 112A and the segment 113A for selective detachment therebetween. Tear line 118B is defined between the removable portion 112B and the segment 113B for selective detachment therebetween. Tear line 120A is defined between the removable portion 114A and the segment 115A for selective detachment therebetween. Tear line 120A is defined between the removable portion 113A and the segment 115A for selective detachment therebetween. In the present example, removable portions 112A and 112B are lateral portions and removable portions 114A and 114B are end portions. In an embodiment, the article 100 includes only one removable portion. In an embodiment, the article 100 includes more removable portions extending from segments of the perimeter 104 than those illustrated in FIG. 6.

In the example shown here, removable portions 112A and 112B include respective inner tear lines I, II, III, IV and V defining respective parts thereof. In this example, removable portion 112A includes removable parts 122A, 124A, 126A, 128A, 130A, and 132A and removable portion 112B includes removable parts 122B, 124B, 126B, 128B, 130A, and 132B. In an embodiment, article 100 does not include lateral tear lines 118A and 118B and only includes the inner lines in order to provide removing selective parts of the removable portions.

In an embodiment, the removable portions and removable parts of sanitary article 100 include indicia for providing the user to selectively remove portions and/or parts based on suggested configurations or preference.

Sanitary article 100 can be provided in a variety of suitable sizes and configurations.

The skilled artisan will readily appreciate that tear lines include without limitation weak lines, perforated lines which may or may not include dotted lines for allowing the user to tear the portions at each side of the tear line along the dotted line as is known in the art.

The various features described herein can be combined in a variety of ways within the context of the present disclosure so as to provide still other embodiments. As such, the embodiments are not mutually exclusive. Moreover, the embodiments discussed herein need not include all of the features and elements illustrated and/or described and thus partial combinations of features can also be contemplated. Furthermore, embodiments with less features than those described can also be contemplated. It is to be understood that the present disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been provided hereinabove by way of non-restrictive illustrative embodiments thereof, it can be modified, without departing from the scope, spirit and nature thereof and of the appended claims.

What is claimed is:

1. A sanitary article to be worn by a wearer and positioned between an undergarment of the wearer and the body of the wearer, the sanitary article comprising:
 a longitudinal main body bounded by a perimeter defining opposite ends and opposite lateral margins running along the length of the main body and comprising a body contacting surface and an opposite outer surface;
 a pair of lateral wing/flap portions contiguous with the main longitudinal body, each of the lateral portions extending beyond a respective one of the lateral margins thereby defining a respective width thereof and extending along a segment of the respective one of the lateral margins thereby defining a respective length thereof, wherein each of the lateral portions defines a respective free edge, each of the lateral portions comprising garment contacting portion having an adhesive for adhesively contacting the undergarment of the wearer, each lateral portion extending beyond a crotch portion of the undergarment to be flipped thereunder and adhered to an outer surface of the undergarment opposite the body contacting surface thereof; and
 a respective longitudinal lateral tear line formed between each of the lateral portions and the respective adjacent margin providing for fully removing each of the lateral portions from the main body portion, wherein the longitudinal lateral tear line provides for detaching the lateral portion along the length thereof without disturbing the physical integrity of the adjacent margin; and
 respective inner tear lines formed within each of the lateral portions extending from the longitudinal lateral tear line to the free edge thereby defining at least three sub-parts of the lateral portion comprising front and rear sub-parts and a median sub-part therebetween, wherein the inner tear lines provide from detaching one or more of the sub-parts of the lateral portion therefrom thereby reducing the size length thereof along the segment of the respective one of the lateral margins or at least front and rear shorter and spaced apart wing/flaps.

2. A sanitary article according to claim 1, wherein each of the sub-parts comprises respective indicia.

3. A sanitary article according to claim 1, wherein the body contacting surface is liquid pervious.

4. A sanitary article according to claim 1, wherein the outer side of the main body is liquid impervious.

5. A sanitary article according to claim 1, wherein the outer side is a garment contacting side.

6. A sanitary article according to claim 5, wherein the outer side comprises an adhesive for adhering to a garment.

\* \* \* \* \*